United States Patent [19]

Kanner et al.

[11] Patent Number: 4,558,146

[45] Date of Patent: Dec. 10, 1985

[54] PROCESS FOR PREPARING VINYLAMINOSILANES

[75] Inventors: Bernard Kanner, West Nyack; Jennifer M. Quirk, Bedford Hills; Arthur P. De Monte, Brooklyn, all of N.Y.; Kunj R. Mehta, Parkersburg, W. Va.

[73] Assignee: Union Carbide Corporation, Danbury, Conn.

[21] Appl. No.: 697,122

[22] Filed: Jan. 31, 1985

[51] Int. Cl.$^4$ .............................. C07F 7/08; C07F 7/10
[52] U.S. Cl. .................................................... 556/410
[58] Field of Search ......................................... 556/410

[56] References Cited

U.S. PATENT DOCUMENTS

| | | | |
|---|---|---|---|
| 2,637,738 | 5/1953 | Wagner | 260/448.2 |
| 2,721,873 | 10/1955 | MacKenzie et al. | 556/410 X |
| 2,823,218 | 2/1958 | Speier et al. | 260/448.2 |
| 4,469,881 | 9/1984 | Arkles | 556/410 X |

FOREIGN PATENT DOCUMENTS 57-04995  1/1982  Japan ........................... 556/410 UX

OTHER PUBLICATIONS

E. Lukevics, *Russ. Chem. Rev.*, 46, 264 (1977).

*Primary Examiner*—Paul F. Shaver
*Attorney, Agent, or Firm*—Paul W. Leuzzi, II

[57] ABSTRACT

A process for preparing vinylaminosilanes in which an aminosilane of the formula $HSi(NRR')_x (R'')_{3-x}$ is reacted with an alkyne of the formula $R'''C\equiv CH$ in which R and R'' are each saturated or unsaturated aliphatic hydrocarbon radicals or an aromatic hydrocarbon radical, R' and R''' are the same or different and are each hydrogen or R and x is an integer from 1 to 3, in the presence of a platinum hydrosilation catalyst at reaction temperatures above about 180° C.

12 Claims, No Drawings

PROCESS FOR PREPARING VINYLAMINOSILANES

BACKGROUND OF THE INVENTION

1. Field of the Invention

The present invention relates to an improved process for the preparation of vinylaminosilanes and, in particular, to a hydrosilation process for producing a high yield of vinylaminosilanes of high purity.

2. Description of the Prior Art

The hydrosilation reaction was discovered about 1947 and, over the years, has become one of the best known and most widely practiced reactions in organosilicon chemistry. It enjoys a broad spectrum of large scale commercial applications and has been the subject of thousands of publications and extensive reviews, including the following monographs:

E. Lukevics and M. G. Voronkov, Organic Insertion Reactions of Group II Elements, Consultants Bureau, N.Y., 1966;

C. Eaborn and R. W. Boh, Organometallic Compounds of the Group IV Elements, Dekker, N.Y., 1968, Vol. I;

M. G. Pomerantseva et al, Preparation of Carbafunctional Organosilanes by an Addition Reaction, Moscow, 1971;

E. Lukevics, Russ. Chem Rev., 46, 264 (1977) and

E. Lukevics et al, J. Organometal Chem. Library 5, 1977, pp. 1-179

Various classes of platinum compounds have been found to be effective hydrosilation catalysts. Chloroplatinic acid, which is a soluble form of platinum, has proved to be an especially effective hydrosilation catalyst, as disclosed in U.S. Pat. No. 2,823,218 issued Feb. 11, 1958. It has also been reported that disilazanes, such as 1,3-dihydrodisilazane and cyclosilazanes, such as tetramethylcyclotetrasilazane, undergo slow catalytic hydrosilation with vinyl unsaturated compounds in the following articles:

K. A. Andrianov et al, Izv. Akad. Nauk SSSR, Ser, Khim. 1968, pp. 351-6;

K. A. Andrianov et al, Ibid, 1969, pp. 1539-45;

E. P. Lebedev and V. O. Reikhsfel'd, Zhur, Obshch. Khim, 38, 655, (1968) and

E. P. Lebedev and V. O. Reikhsfel'd, Ibid, 40, 1082, (1970)

It has also been reported that mono- bis- and tris(-dialkylamino)silanes show little or no reactivity for hydrosilation. That lack of reactivity has been attributed to the inability of such alkylaminosilanes to form intermediate catalytic complexes with a platinum hydrosilation catalyst, W. B. Dennis and J. L. Speier, J. Org Chem. 35, 3879 (1970).

It has been more recently disclosed that a hydrosilation mechanism is possible for the reaction of hydroaminosilanes with arylacetylenes, I. M. Gverdtsiteli et al, Soobshch Akad. Nauk Gruz. SSR, 84, 381 (1976) and I. M. Gverdtsiteli et al, Tezisy Dokl-Vses. Konf. Khim. Atsetilena, 5th, 1975, 172. It was reported therein that dimethyl diethylamino silane, diethyl morpholino silane and methyl diethylamino morpholino silane reacted with diphenylacetylenes (RC≡RC) via a hydrosilation mechanism to provide diphenylvinyl-substituted aminosilanes in yields only to 40 to 50 percent of the theoretical. It was also reported that attempted hydrosilations with monophenyl acetylene (RC≡CH) resulted in a dehydrocondensation reaction which yielded an acetylenic, rather than a vinyl, adduct. Such arylacetylene reactions were typically run at reaction temperatures between about 20° to 100° C.

Vinylaminosilanes are well known to the art as illustrated in U.S. Pat. No. 3,485,857 issued Dec. 23, 1969 and U.S. Pat. No. 3,445,425, issued May 20, 1969. Such compounds are considered to be useful intermediates and highly reactive coupling agents.

SUMMARY OF THE INVENTION

The present invention is a process for preparing vinylaminosilanes by reacting an aminosilane of the general formula I:

$$HSi(NRR')_x(R'')_{3-x} \qquad [I]$$

an alkyne of the general formula II:

$$R'''C\equiv CH \qquad [II]$$

wherein R' and R''' are the same or different and are each hydrogen, a saturated or unsaturated aliphatic hydrocarbon radical or an aromatic hydrocarbon radical, R and R'' are the same or different and are each a saturated or unsaturated aliphatic hydrocarbon radical or an aromatic hydrocarbon radical and x is an integer from 1 to 3, in the presence of a platinum hydrosilation catalyst at a reaction temperature greater than 180° C. to form a vinylaminosilane of the general formula III:

$$R'''CH=CHSi(NRR')_x(R'')_{3-x}$$

wherein R, R', R'' and R''' are as before.

It has been found that the temperature of the reaction should be maintained at least about 180° C. to provide satisfactory yields of the desired vinylaminosilane product. At lower reaction temperatures the yields of desired vinylaminosilanes are substantialy reduced. In addition, it is an important feature of the process of the invention that the amount of undesired by-products is very low. This is contrast to reactions of trichlorosilane and most trialkoxysilanes in which substantial amounts of bis(silyl)ethane are produced, when a platinum hydrosilation catalyst is employed, such as chloroplatinic acid, as reported in Japanese Pat. No. 57-4995, issued Jan. 11, 1982.

DESCRIPTION OF THE PREFERRED EMBODIMENTS

The aminosilane reactants employed in the present invention are of the general formula (I):

$$HSi(NRR')_x(R'')_{3-x} \qquad [I]$$

wherein R' is hydrogen, a saturated or unsaturated aliphatic hydrocarbon radical, or an aromatic hydrocarbon radical, R and R'' are each a saturated or unsaturated aliphatic hydrocarbon radical or an aromatic hydrocarbon radical and x is an integer from 1 to 3.

Typical examples of R, R' and R'' are alkyl radicals, such as methyl, ethyl, propyl, isopropyl, butyl, isobutyl, pentyl, isopentyl, neopentyl, hexyl, octyl, dodecyl, octadecyl, 3-methylheptyl, 6-butyloctadecyl, tertiary butyl and 2,2-diethylpentyl; alkenyl radicals, such as allyl, hexenyl, butenyl, 3-octenyl, 4,9-octadecadienyl and 4-nonenyl; alkynyl radicals, such as propynyl, heptynyl, butynyl, decynyl and alkenynyl radicals, such as 1-penten-3-ynyl and 2-ethyl-1-buten-3-ynyl; cycloaliphatic radicals, such as cyclobutyl, cyclopentyl, cyclohexyl, cycloheptyl, propylcyclohexyl, 2,4-dimethylcyclopentyl, cyclohexenyl, bicyclo (3.1.0) hexyl, tricyclo-(3.2.1.1$^{3,8}$)-5-nonenyl, spiro[4.5]decyl, dispiro(4.1.4.2)-1-tridecenyl, decahydronaphthyl, 2.3-dihydroindyl and 1,2,3,4-tetrahydronaphthyl and aryl radicals, such as phenyl, tolyl, xylyl, 3-ethylphenyl, naphthyl, pentaphenyl, 3,4-methylethyl-phenyl, 2-phenyl-octyl, 3-methyl-2-(4-isopropylphenyl)heptyl, benzyl, 2-ethyl-tolyl, 2-ethyl-p-cymenyl, diphenyl-methyl, 4,5-diphenylpentyl, 4-m-terphenyl, 9,9'-bifluoryl and beta-phenylethyl.

In addition R and R' can together form a heterocyclic radical with the nitrogen (N) of formula I, such as a piperidino, piperazino or morpholino radical or an alkyl substituted heterocyclic radical or the like.

Typical examples of the aminosilanes of this invention include:

HSi[N(CH$_3$)(C$_2$H$_5$)]$_3$;
HSi[N(C$_2$H$_5$)$_2$]$_3$;
HSi[N(C$_3$H$_7$)$_2$]$_3$;
HSi[N(CH$_3$)(CH$_2$CH$_2$CH$_2$CH$_3$)]$_3$;
HSi[N(CH$_3$)(C$_{12}$H$_{25}$)]$_3$;
HSi[N(C[CH$_3$]$_3$)$_2$]$_2$CH$_3$;
HSi[N(CH$_3$)(CH$_2$CH=CH$_2$)]$_2$C$_2$H$_5$;
HSi[N(CH$_3$)(CH$_2$C≡CCH$_3$)]$_2$C$_3$H$_7$;
HSi[N(CH$_3$)$_2$]$_2$C$_2$H$_5$;
HSi[N(CH$_3$)$_2$]$_2$C$_5$H$_{11}$;

HSi[N(CH$_3$) (CH⟨CH$_2$—CH$_2$⟩⟨CH$_2$—CH$_2$⟩CH$_2$)]$_3$

HSi[N(CH$_3$)(C$_6$H$_5$)]$_3$;
HSi[N(CH$_6$H$_5$)$_2$]$_3$;

HSi[N(CH$_3$) (—⟨cyclohexyl⟩—CH$_3$)]$_2$CH$_3$;

HSi[N(CH$_3$) (—⟨decalin⟩)]$_3$;

HSi[N(CH$_3$) (—⟨bicyclohexyl⟩)]$_3$;

HSi[N(CH$_3$) (—CH$_2$—⟨cyclohexyl⟩)]$_3$;

HSi[N(CH$_3$) (—⟨cyclohexyl⟩—CH$_2$—⟨cyclohexyl⟩)]$_3$;

HSi[N(CH$_3$)$_2$](CH$_3$)$_2$
HSi[N(CH$_3$)$_2$]$_2$CH$_3$
HSi[N(CH$_3$)$_2$]$_3$
HSi(C$_2$H$_5$)[N(CH$_3$)$_2$]$_2$;
HSi(C$_3$H$_7$)[NCH$_3$)$_2$]$_2$;
HSi(CH$_2$CH$_2$CH$_2$CH$_3$)[N(CH$_3$)$_2$]$_2$;
HSi(C$_{12}$H$_{25}$)[N(C$_3$H$_7$)$_2$]$_2$;
HSi(C$_{13}$H$_{27}$)[N(CH$_3$)$_2$]$_2$
HSi(CH$_2$CH=CHCH$_2$CHC≡CCH$_3$)[N(CH$_3$)]$_2$;

HSi(—CH$_2$CH$_2$—⟨cyclohexyl⟩—)[N(CH$_3$) (C$_2$H$_5$)]$_2$;

HSi(—⟨bicyclohexyl⟩—)[N(CH$_3$)$_2$]$_2$;

HSi(—⟨bicyclohexyl⟩—)$_2$
|
N(CH$_2$CH$_3$) (CH$_3$)

CH$_2$CH=CH$_2$
|
HSiN(CH$_3$)$_2$,
|
CH$_3$

In general the preferred aminosilanes of the invention are those in which R' is H and lower alkyl, and R and R" are each alkyl or, together with N, are saturated heterocyclic. Especially preferred aminosilanes of the invention include dimethylaminodimethylsilane; bis(dimethylamino)methylsilane, tris(piperidino)silane and, particularly, tris(dimethylamino)silane. The alkynes of the invention which, in the presence of the hydrosilation catalyst of the invention, form vinyl adducts with the aminosilanes of the invention, have the general formula II:

R'''C≡CH wherein R''' is hydrogen and an aliphatic or aromatic hydrocarbon radical. Typical examples of R''' radicals include: alkyl radicals having from about 1 to 20 carbon atoms such as methyl, ethyl, propyl, isopropyl, butyl, pentyl, hexyl, octyl, dodecyl, heptadecyl and eicosyl radicals, aryl radicals, such as phenyl, tolyl, xylyl, naphthyl, beta-phenylethyl, benzyl, 2-phenyl-octyl, diphenyl-methyl and like radicals and cycloaliphatic radicals, such as cyclobutyl, cyclopentyl, cyclohexyl, propycyclohexyl, bicyclo[3.1.0]hexyl, spiro[4.5]decyl and like radicals.

The preferred alkynes of the invention are acetylene, 1-hexyne, 1-octyne and phenylacetylene.

In general, the molar ratio of the aminosilane reactant to the alkyne reactant should be 1:1 (or the stoichiometric ratio) to provide the best yields.

The reaction is carried out in the presence of a platinum hydrosilation catalyst of the invention. The platinum catalyst can be employed in a broad spectrum of forms. The catalyst can be platinum metal, either alone or on a support, such as carbon black or alumina. Soluble compounds of platinum or complexes of platinum are also employed as the platinum catalyst.

Typical soluble compounds of platinum are hexachloroplatinic acid and platinum (II) 2,4-pentanedionate. Solutions of hexachloroplatinic acid in organic solvents; such as alcohols, including methanol, ethanol, and isopropanol; ketones, such as cyclohexanone;

ethers, as dimethyl ether of ethylene glycol or diethyleneglycol and esters as ethyl acetate or methyl benzoate, can also be utilized.

Platinum complexes combined with unsaturated compounds as ethylene, cyclohexene, styrene, alkylethylenes or such platinum complexes with phosphines, phosphines on polymeric carriers, cyclopropane and sulphoxides, can also be utilized.

If desired, bivalent and quadrivalent platinum complexes may also be employed. Platinum complexes on inorganic or organic polymeric carriers and polymeric platinum chelates are also possible forms for the platinum hydrosilation catalyst. Other suitable forms of platinum catalysts will be apparent to those skilled in the art.

Usually, best results are obtained, and accordingly, it is preferred to employ as the hydrosilation catalyst, chloroplatinic acid, platinum (II) 2,4-pentanedionate or a platinum phosphine complex, as bis(triphenylphosphine)platinum (II) chloride and tetrakis(triphenylphosphine)platinum.

In general, the catalyst is employed in sufficient amounts to complete the reaction. Because platinum catalysts are expensive, it is usually best to employ them in amounts not in excess of that which is required to provide satisfactory yields. Accordingly, for this and other purposes it is preferred to employ from about $1 \times 10^{-5}$ mole percent $5 \times 10^{-2}$ mole percent of platinum hydrosilation catalyst of the invention based on the amount of aminosilane to be reacted. The reaction temperature at which the process of the invention is carried out is very important. At reaction temperatures below about 180° C. it has been found that substantially reduced yields of vinylsilane adducts are obtained. At temperatures above about 180° C., however, the silicon-hydrogen bond adds readily across the alkyne bond in the presence of the hydrosilation catalyst to yield the vinylsilanes of the invention as follows:

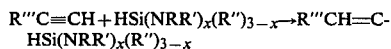

where R, R′, R″, R‴ and x are as before.

The amount of undesired by-products produced by the inventive process, such as bis(silyl)ethane, is insignificant, as compared to hydrosilation reactions of trichlorosilane and most trialkoxysilanes, which yield both vinylsilane and bis(silyl)ethane, when chloroplatinic acid is the hydrosilation catalyst.

While the particular reasons for the enhanced reactivity of the aminosilanes of the invention toward hydrosilation at the elevated reaction temperatures of at least about 180° C. is not completely understood, it is believed that at such higher temperatures an intermediate platinum-silicon catalytic complex is more readily formed, while at lower temperatures the aminosilane forms the desired catalytic intermediate complex, very slowly.

Another important and unexpected feature of the present process is that there does not seem to be any significant catalyst degradation at the elevated reaction temperatures. That feature is evidence that the platinum aminosilane catalytic intermediates are relatively stable and contribute significantly to the high efficiency of the instant process. The vinylaminosilane product yield of the instant process is unusually high. Usually product yields are at least about 90% of theoretical and, most often, over 95% theoretical.

In general, the upper reaction temperature of the present invention is determined by the decomposition temperature of either the starting materials or the reaction product. For most purposes it is preferred to maintain the reaction temperature from about 220° C. to 250° C.

The reaction pressure is not critical. The process is best conducted at atmospheric or superatmospheric pressures. If desired, the reaction is conducted at alkynyl gas inlet pressures which can be greater than atmospheric and preferably on the order from about 100 to 150 psig.

The reaction time is not a significant factor in the process. In general, the reaction is completed in from about ½ to 8 hours, and, usually, in from about 2 to 4 hours.

The reaction may be carried out in the absence or presence of a reaction solvent. If it is desired to enhance the solubility of the reactants or to provide a heat sink to help maintain proper temperature control, a solvent can be employed. Typical reaction solvents include hydrocarbon solvents, such as octane, xylene or, preferably, triisopropylbenzene.

In order to conduct the process of the invention the reactants are added in any appropriate order. Generally, the platinum catalyst is added to the aminosilane reactant, the reaction mix heated to the desired reaction temperature and then the alkyne reactant, such as acetylene gas, is fed into the reaction at a constant rate until addition is complete. The product is recovered and analyzed by conventional procedures. Where all the reactants are liquids, the reactants are added to an autoclave, the autoclave is sealed and the contents heated until the reaction is complete.

The following examples illustrate certain preferred embodiments of the invention under laboratory conditions. They are not intended to limit the scope of the invention.

EXAMPLE 1

A 500 ml 3-neck flask was equipped with a stopper, Claisen adapter, thermometer and stirring bar. A septum was wired to the Claisen adapter and a water condenser and a Dewar condenser attached to the side arm. Into the flask was introduced 100 g (0.49 mol.) of triisopropylbenzene solvent and 30 g (0.19 mol.) of tris(dimethylamino)silane. Into this mix was added 60 ppm (120 ul of 15 mg Pt/ml) chloroplatinic acid. The reaction mix was heated to 235° C. in an oil bath and acetylene was fed into the reaction mix with a stainless steel twelve (12) inch needle at a rate of 75-100 cc/min. with a back pressure of 4-5 psig. After two hours the hydrosilation reaction was complete as determined by GPC. The single product formed was vinyltris(dimethylamino)silane in amounts greater than 92% of the theoretical yield.

COMPARATIVE EXAMPLE I

The process was carried out as in Example 1; however, a reaction temperature of 150° C., and a reaction time of 8 hours were used. After 8 hours, no reaction product was formed.

EXAMPLE 2

The reaction was carried out as in Example I, except that bis(triphenylphosphine)platinum (II) chloride was used as the platinum hydrosilation catalyst. The single product formed was vinyltris(dimethylamino)silane in a yield greater than 90% of theoretical.

EXAMPLE 3

A two liter stirred batch reactor was purged with nitrogen gas and thereafter charged with 840 g (5.22 moles) of tris(dimethylamino)silane and 5 ppm hexachloroplatinic acid. The reactor was then pressurized to approximately 5 psig with nitrogen gas and heated to approximately 250° C. The acetylene inlet feed was started and maintained at 100 psig. The reaction temperature was maintained at 250° C. After four hours the acetylene flow was stopped, the reaction mix cooled and the reaction products analyzed. Vinyltris(dimethyl-)amino)silane was the single major product at 90% of theoretical. Ethyltris(dimethylamino)silane and 1,2-bis(-trisdimethylamino)silylethane by-products were formed in amounts less than 0.5% each. Vinyltris(dimethylamino)silane polymer was also formed in an amount of 7-8%.

EXAMPLE 4

The reaction was carried out as in Example 3; however, the acetylene pressure was increased to 150 psig and the reaction temperature was maintained at 240° C. Vinyltris(dimethylamino)silane was the single major product at a yield of 85% theoretical. Ethyltris(dimethylamino)silane and 1,2-bis(trisdimethylamino)silylethane were also formed, each in approximately a 2 to 3% yield. Vinyltris(dimethylamino)silane was also formed in approximately 10% yield.

EXAMPLE 5

The reaction was run in accordance with the procedure of in Example 3; however, the acetylene pressure was 120 psig and the reaction temperature was maintained at 230° C. The single major product was vinyltris(dimethylamino)silane in a 85% yield. Ethyltris(dimethylamino)silane and 1,2-bis(trisdimethylamino)-silylethane were each formed in amounts of approximately 1%. Vinyltris-(dimethylamino)silane polymer was also formed in an amount of approximately 10%.

What is claimed is:

1. Process for preparing vinylaminosilanes by reacting an aminosilane of the general formula I:

$$HSi(NRR')_x(R'')_{3-x} \quad [I]$$

with an alkyne of the general formula II:

$$R'''C{\equiv}CH \quad [II]$$

wherein R' and R''' are the same or different and are each hydrogen, a saturated or unsaturated aliphatic hydrocarbon radical or an aromatic hydrocarbon radical, R and R'' are the same or different and are each a saturated or unsaturated aliphatic hydrocarbon radical or an aromatic hydrocarbon radical and x is an integer from 1 to 3, in the presence of a platinum hydrosilation catalyst at a reaction temperature greater than 180° C. to form a vinylaminosilane of the general formula III:

$$R'''CH{=}CHSi(NRR')_x(R'')_{3-x}$$

wherein R, R', R'', R''' and x are as before.

2. The process of claim 1 in which the aminosilane is tris(dimethylamino)silane.

3. The process of claim 1 in which the alkyne is acetylene.

4. The process of claim 1 in which the catalyst is chloroplatinic acid.

5. The process of claim 1 in which the catalyst is bis(triphenylphosphine)platinum (II) chloride.

6. The process of claim 1 in which the reaction temperature is from about 220° C. to 250° C.

7. The process of claim 1 in which the molar ratio of aminosilane to alkyne is about 1:1.

8. The process of claim 1 in which the catalyst is employed in amounts from $1.0 \times 10^{-5}$ mole percent to $5.0 \times 10^{-2}$ mole percent based on the aminosilane.

9. The process of claim 1 in which the reaction is carried out in a hydrocarbon solvent.

10. The process of claim 9 in which the solvent is triisopropylbenzene.

11. The process of claim 1 in which the alkyne is added to the reaction at greater than atmospheric pressure.

12. The process of claim 1 in which the alkyne is added to the reaction at pressures from about 100 to 150 psig.

* * * * *